(12) United States Patent
Kim

(10) Patent No.: US 11,925,897 B2
(45) Date of Patent: Mar. 12, 2024

(54) DEVICE FOR REMOVING BIOMATERIAL

(71) Applicant: ELECTRONICS AND TELECOMMUNICATIONS RESEARCH INSTITUTE, Daejeon (KR)

(72) Inventor: Jin Tae Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 288 days.

(21) Appl. No.: 17/500,368

(22) Filed: Oct. 13, 2021

(65) Prior Publication Data

US 2022/0347625 A1    Nov. 3, 2022

(30) Foreign Application Priority Data

Apr. 28, 2021    (KR) .................. 10-2021-0054989

(51) Int. Cl.
*B01D 53/02* (2006.01)
*B01D 47/02* (2006.01)
(Continued)

(52) U.S. Cl.
CPC .......... *B01D 53/30* (2013.01); *B01D 47/021* (2013.01); *B01D 53/06* (2013.01); *G01N 21/94* (2013.01); *B01D 2257/91* (2013.01)

(58) Field of Classification Search
CPC ............. A61L 2209/14; A61L 2209/22; B01D 2257/91; B01D 47/021; B01D 53/06;
(Continued)

(56) References Cited

U.S. PATENT DOCUMENTS 6,224,655 B1 * 5/2001 Messier ............. B01D 46/0028
55/497
8,277,644 B2    10/2012 Kim et al.
(Continued)

FOREIGN PATENT DOCUMENTS

KR           10-1720695 B1     4/2017
KR    10-2018-0090007 A        8/2018
(Continued)

OTHER PUBLICATIONS

Translation of KR102144259 (Year: 2020).*
(Continued)

*Primary Examiner* — Christopher P Jones
(74) *Attorney, Agent, or Firm* — LRK PATENT LAW FIRM

(57) ABSTRACT

Provided is a biomaterial removing device including an air injection part, a first processing part spaced apart from the air injection part, and a second processing part spaced apart from the air injection part with the first processing part therebetween, wherein the first processing part includes a first biomaterial removing part configured to remove biomaterials included in air collected from the air injection part and a first monitoring part, and the second processing part includes a second biomaterial removing part configured to remove the residual biomaterials and a second monitoring part, wherein the first biomaterial removing part includes a dry air purifier, the second biomaterial removing part includes a wet air purifier, and the first biomaterial removing part and the second biomaterial removing part each include an image sensor.

20 Claims, 19 Drawing Sheets

(51) Int. Cl.
    *B01D 53/06*     (2006.01)
    *B01D 53/30*     (2006.01)
    *G01N 21/94*     (2006.01)

(58) Field of Classification Search
    CPC ........... B01D 53/30; F24F 11/39; F24F 8/108;
    G01N 15/1434; G01N 15/1459; G01N
    15/1463; G01N 15/1484; G01N
    2015/0038; G01N 2015/0065; G01N
    2015/1481; G01N 21/8483; G01N 21/94;
    Y02A 50/20
    See application file for complete search history.

(56) References Cited

U.S. PATENT DOCUMENTS 9,155,825 B2 * 10/2015 Kelly .............. A61M 1/362265

| | | | |
|---|---|---|---|
| 2007/0207551 A1* | 9/2007 | Glensbjerg | G01N 15/1475 |
| | | | 422/105 |
| 2013/0137082 A1 | 5/2013 | Park et al. | |
| 2020/0330986 A1 | 10/2020 | Yang et al. | |
| 2020/0330989 A1 | 10/2020 | Masuhara et al. | |
| 2022/0347625 A1* | 11/2022 | Kim | G01N 21/94 |

FOREIGN PATENT DOCUMENTS

KR     10-1963328 B1     3/2019
KR     10-2144259 B1     8/2020

OTHER PUBLICATIONS

F. Wu et al., "Layered material platform for surface plasmon resonance biosensing", Scientific Reports, 9:20286, UNIST, Dec. 30, 2019.

* cited by examiner

DEVICE FOR REMOVING BIOMATERIAL

CROSS-REFERENCE TO RELATED APPLICATION

This U.S. non-provisional patent application claims priority under 35 U.S.C. § 119 of Korean Patent Application No. 10-2021-0054989, filed on Apr. 28, 2021, the entire content of which is hereby incorporated by reference.

BACKGROUND

1. Field of the Invention

The present disclosure herein relates to a biomaterial removing device capable of real-time monitoring.

2. Description of Related Art

Recently, the issue of transmission of biomaterials, such as viruses or bacteria, due to respiratory droplets from respiratory organs has occurred. When an infected person coughs, sneezes, or talks, respiratory droplets (saliva droplets) that come out of the mouth of the infected person may float in the air and may be transmitted to uninfected people through their mucous membranes of eyes, noses, or mouths. Therefore, it is required to develop a biomaterial removing system for preventing biomaterials such as viruses or bacteria from being transmitted through the air.

SUMMARY

The present disclosure provides a device for removing biomaterials in air, which is capable of real-time monitoring.

The purposes of the present disclosure are not limited to the above-mentioned purposes, and other purposes not mentioned would be clearly understood by those skilled in the art from the disclosure below.

An embodiment of the inventive concept provides a biomaterial removing device including an air injection part, a first processing part spaced apart from the air injection part in a first direction, and a second processing part spaced apart from the air injection part with the first processing part therebetween, wherein the first processing part includes a first biomaterial removing part configured to remove biomaterials included in air collected from the air injection part and a first monitoring part configured to analyze residual biomaterials that have passed through the first biomaterial removing part among the biomaterials, and the second processing part includes a second biomaterial removing part configured to remove the residual biomaterials and a second monitoring part configured to analyze whether at least one biomaterial among the residual biomaterials has passed through the second biomaterial removing part, wherein the first biomaterial removing part includes a dry air purifier, the second biomaterial removing part includes a wet air purifier, and the first biomaterial removing part and the second biomaterial removing part each include an image sensor.

In an embodiment, the biomaterial removing device may further include rotating parts arranged on both ends of the dry air purifier, wherein the dry air purifier may be continuously moved due to rotation of the rotating parts, and the dry air purifier may extend in a second direction intersecting the first direction.

In an embodiment, the dry air purifier may include a plurality of laminated nonwoven fabric sheets.

In an embodiment, the wet air purifier may include a container configured to be provided with a solution, an air injection pipe for injecting air into the solution, and an air discharging pipe, which is connected to the container and discharges air from which the at least one biomaterial among the residual biomaterials has been removed, wherein the at least one biomaterial may be collected in the solution.

In an embodiment, the biomaterial removing device may further include a solution discharging part and a pump between the container and the solution discharging part.

In an embodiment, the biomaterial removing device may further include an air suction part, and the solution discharging part may deliver an extracted solution in which the at least one biomaterial is collected to the second monitoring part, wherein the air suction part may include a vent hole.

In an embodiment, the second monitoring part may further include a nano-optical sensor, wherein the nano-optical sensor may include a substrate and an upper layer.

In an embodiment, the upper layer may include at least one of a semiconductor material, transition metal dichalcogenide, graphene, or hexagonal boron nitride (hBN).

In an embodiment, the upper layer may include InGaAsP.

In an embodiment, the biomaterial removing device may further include a lower layer between the substrate and the upper layer, wherein the lower layer may include a plurality of nano-holes penetrating the lower layer and partially exposing an upper surface of the substrate.

In an embodiment, a diameter and interval of the nano-holes may change in the first direction.

In an embodiment, the substrate may include a silicon oxide, and the lower layer may include silicon.

In an embodiment, the upper layer may have a circular shape in a plan view.

In an embodiment, the upper layer may include a plurality of holes penetrating the upper layer and partially exposing an upper surface of the substrate, wherein the holes may be arranged adjacent to an outer circumference of the upper layer.

In an embodiment, the second monitoring part may further include a sensor substrate, wherein the sensor substrate may include a vacuum space therein, and the nano-optical sensor may be arranged in the vacuum space.

In an embodiment, the first monitoring part may include a nozzle into which air that has passed through the first biomaterial removing part is injected and a transparent substrate on a lower surface of the nozzle, and the image sensor may be arranged on a lower surface of the transparent substrate.

In an embodiment, the residual biomaterials included in air may adhere to an upper surface of the transparent substrate, and the image sensor may capture an image of the residual biomaterials.

In an embodiment, the image sensor may be a complementary metal oxide silicon (CMOS) image sensor.

In an embodiment, the biomaterial removing device may further include a pipe between the air injection part and the first processing part, and the air injection part and the first processing part may be connected to each other by the pipe.

In an embodiment, the biomaterial removing device may further include an air discharging part configured to output, to the outside, air from which the residual biomaterials have been removed by the second processing part.

BRIEF DESCRIPTION OF THE DRAWINGS

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Figure 1:
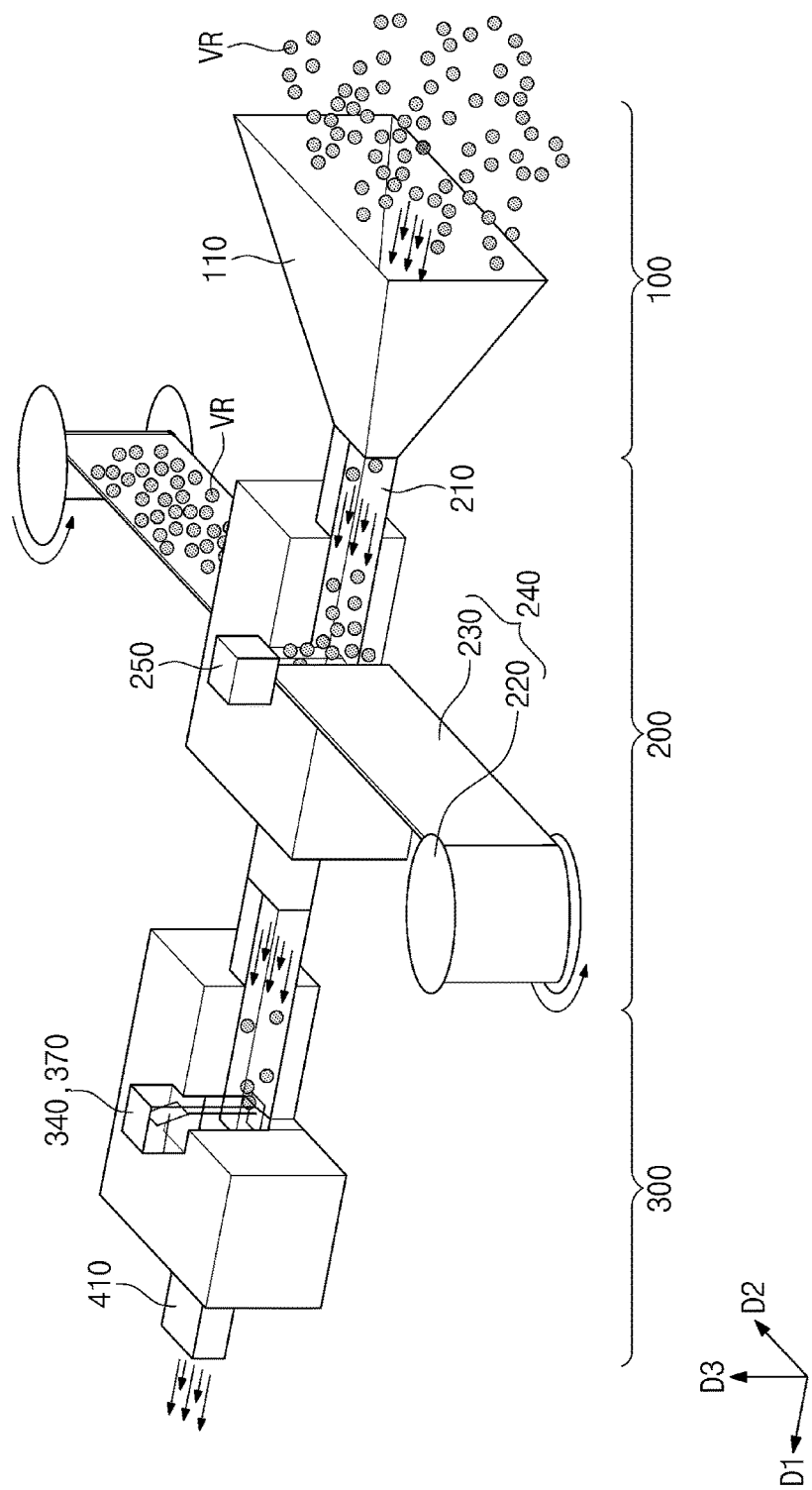
FIG. 1 is a schematic perspective view illustrating a biomaterial removing device according to an embodiment of the inventive concept.

Advantages and features of the inventive concept, and implementation methods thereof will be clarified through following embodiments described with reference to the accompanying drawings. The inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art. Further, the inventive concept is only defined by the scope of claims. Like reference numerals refer to like elements throughout.

The terminology used herein is not for delimiting the embodiments of the inventive concept but for describing the embodiments. The terms of a singular form may include plural forms unless otherwise specified. The term "include," "comprise," "including" or "comprising" specifies an element, a step, an operation and/or an element but does not exclude other elements, steps, operations and/or elements.

In this description, when a film (or layer) is referred to as being "on" another film (or layer), it can be directly on the other film (or layer), or intervening films (or layers) may also be present.

The embodiments of the inventive concept will be described with reference to example cross-sectional views and/or plan views. In the drawings, the dimensions of layers and regions are exaggerated for clarity of illustration. Therefore, the forms of the example drawings may be changed due to a manufacturing technology and/or error tolerance. Therefore, the embodiments of the inventive concept may involve changes of shapes depending on a manufacturing process, without being limited to the illustrated specific forms. Therefore, the regions illustrated in the drawings are merely schematic, and the shapes of the regions exemplify specific shapes of the elements but do not limit the scope of the invention.

The terms used to describe the embodiments of the inventive concept may be interpreted as the meanings known in the art unless the terms are defined differently.

FIG. 1 is a schematic perspective view illustrating a biomaterial removing device according to an embodiment of the inventive concept.

Referring to FIG. 1, the biomaterial removing device according to an embodiment of the inventive concept may include an air injection part 100, a first processing part 200, and a second processing part 300. In addition, the biomaterial removing device according to an embodiment of the inventive concept may further include a pipe 210 arranged between the air injection part 100 and the first processing part 200 and between the first processing part 200 and the second processing part 300. The biomaterial removing device according to an embodiment of the inventive concept may further include an air discharging part 410.

The air injection part 100 may include an air collector 110. External air may be collected by the air collector 110 and may be injected into the biomaterial removing device according to an embodiment of the inventive concept. Here, the external air may include biomaterials VR that are present in a form of droplets. The biomaterials VR may include an infectious agent, for example, viruses, bacteria, and the like. For example, the air collector 110 may have a shape of a funnel. However, an embodiment of the inventive concept is not limited thereto, and the air collector 110 may have various shapes capable of collecting air.

The first processing part 200 may be arranged spaced apart from the air injection part 100 in a first direction D1. The first processing part 200 may be spaced apart from the air injection part 100 with the pipe 210 therebetween. The pipe 210 may connect the air injection part 100 and the first processing part 200. That is, the external air collected through the air injection part 100 may pass through the pipe 210 and may be injected into the first processing part 200. The biomaterials VR included in externally injected air may be removed by the first processing part 200.

The first processing part 200 may include a first biomaterial removing part 240, which removes the biomaterials VR included in air collected from the air injection part 100, and a first monitoring part 250, which analyzes the residual biomaterials VR included in air that has passed through the first biomaterial removing part 240.

Figure 2:
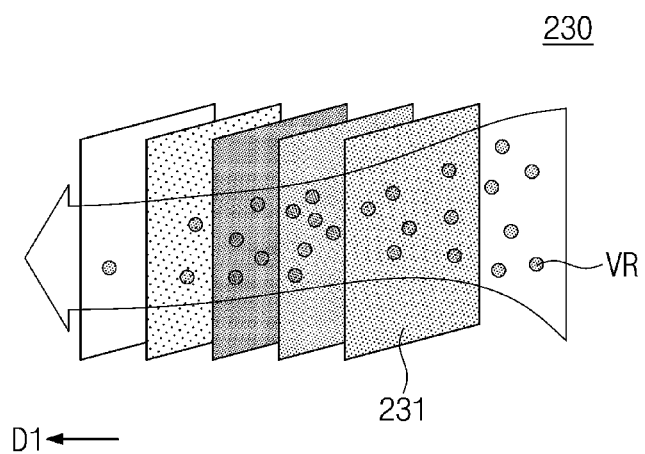
FIG. 2 is a schematic enlarged view of a dry air purifier according to an embodiment of the inventive concept.

FIG. 2 is a schematic enlarged view of a dry air purifier according to an embodiment of the inventive concept.

Referring to FIGS. 1 and 2, the first biomaterial removing part 240 may include a rotating part 220 and a dry air purifier 230. The dry air purifier 230 may extend in a second direction D2 intersecting the first direction D1. For example, the dry air purifier 230 may be a filter. The rotating parts 220 may be arranged on both ends of the dry air purifier 230. For example, the rotating part 220 may have a shape of a roll. The dry air purifier 230 may be continuously moved due to rotation of the rotating part 220. For example, the dry air purifier 230 may be moved in the second direction D2. However, the above description about the direction is merely an example, and an embodiment of the inventive concept is not limited thereto.

The dry air purifier 230 may include a single nonwoven fabric sheet 231 or a plurality of laminated nonwoven fabric sheets 231. For example, when air moves in the first direction D1, the biomaterials VR included in air may be removed by the dry air purifier 230 moving in the second direction D2. In detail, the biomaterials VR included in air that that has passed through the pipe 210 may be adsorbed to the dry air purifier 230. That is, the biomaterials VR may be adsorbed to the dry air purifier 230 adjacent to the pipe 210, and a contaminated portion in the dry air purifier 230 may be moved in the second direction D2 and discarded. A new (i.e., uncontaminated) portion in the dry air purifier 230 may be moved again so as to be adjacent to the pipe 210, and the biomaterials VR included in new air that has newly passed through the pipe 210 may be removed. That is, the dry air purifier 230 may continuously remove the biomaterials VR included in air.

Figure 3:
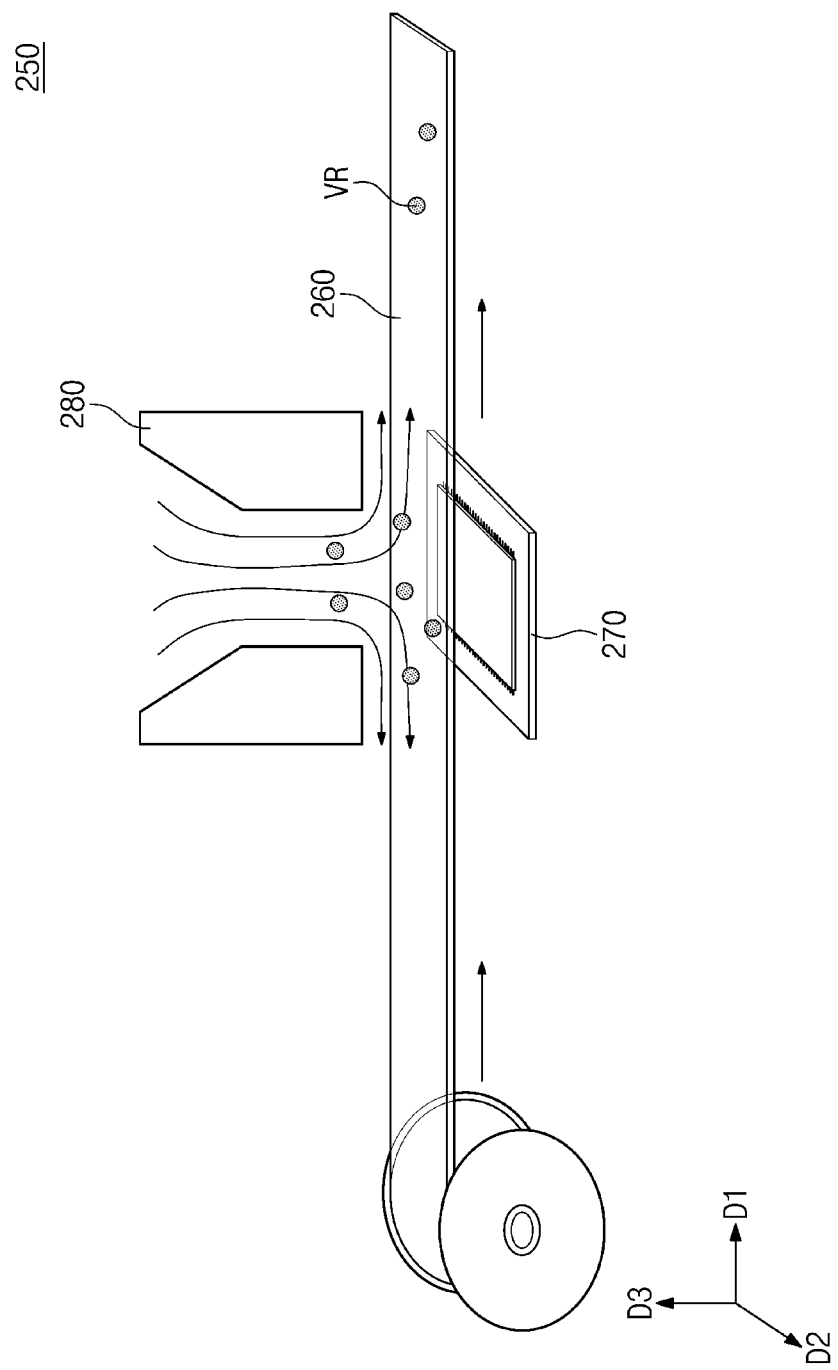
FIG. 3 is a schematic perspective view illustrating a first monitoring part according to an embodiment of the inventive concept.

FIG. 3 is a schematic perspective view illustrating a first monitoring part according to an embodiment of the inventive concept.

Referring to FIGS. 1 and 3, the first monitoring part 250 may include a nozzle 280, a transparent substrate 260, and a first image sensor 270.

The nozzle 280 may be arranged on an upper surface of the transparent substrate 260. The first image sensor 270 may be arranged on a lower surface of the transparent substrate 260. For example, the transparent substrate 260 may be a flexible transparent substrate and may be a consumable cartridge. Air that has passed through the first biomaterial removing part 240 may be injected onto the transparent substrate 260 through the nozzle 280. The residual biomaterials VR that have passed through the first biomaterial removing part 240, among the biomaterials VR, may adhere onto the transparent substrate 260. The transparent substrate 260 is wound in a shape of a roll, and thus may be continuously moved in one direction (e.g., the first direction D1). Accordingly, air may be continuously injected onto the transparent substrate 260, and the transparent substrate 260 to which at least one of the residual biomaterials VR adheres may be moved in one direction (e.g., the first direction D1) and discarded.

The first image sensor 270 may capture an image of air present between the nozzle 280 and the transparent substrate 260, and may analyze whether the biomaterials VR are present in a form of droplets in air. The image captured by the first image sensor 270 may be analyzed by a system, to which an artificial intelligence image analysis method is applied, so as to determine whether biomaterials are present in droplets. For example, the first image sensor 270 may be a complementary metal oxide silicon (CMOS) image sensor.

Referring back to FIG. 1, air that has passed through the first processing part 200 may be moved to the pipe 210 arranged between the first processing part 200 and the second processing part 300 and may be introduced into the second processing part 300.

Figure 4:
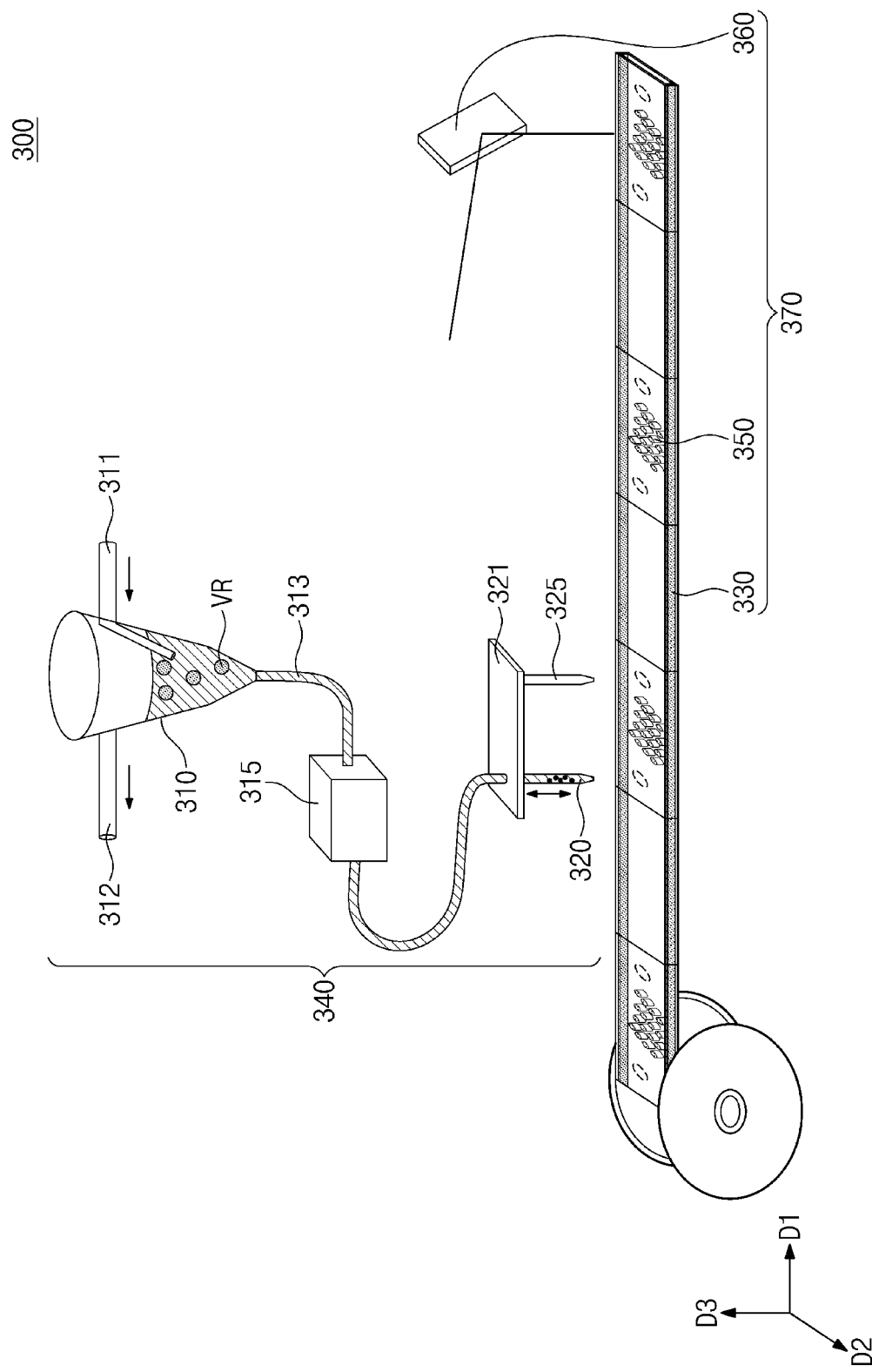
FIG. 4 is a schematic perspective view illustrating a second processing part according to an embodiment of the inventive concept.

FIG. 4 is a schematic perspective view illustrating a second processing part according to an embodiment of the inventive concept.

Referring to FIGS. 1 and 4, the second processing part 300 may include a second biomaterial removing part, which removes the residual biomaterials VR included in air that has passed through the first processing part 200, and a second monitoring part 370, which analyzes the biomaterials VR included in air that has passed through the second biomaterial removing part.

The second biomaterial removing part may include a wet air purifier 340. For example, the wet air purifier 340 may be an air purifier using a solution. The wet air purifier 340 may include a container 310 configured to be provided with a solution, an air injection pipe 311 for injecting air into the solution, an air discharging pipe 312, which is connected to the container 310 and discharges air from which at least one biomaterial VR among the residual biomaterials VR has been removed, a solution discharging part 320, an air suction part 325, and a pump 315 arranged between the container 310 and the solution discharging part 320. The wet air purifier 340 may further include a support substrate 321 for fixing the solution discharging part 320 and the air suction part 325.

Air injected into the solution through the air injection pipe 311 may form bubbles in the solution. The biomaterials VR included in air may be collected in the solution. In detail, at least one of the residual biomaterials VR may be collected in the solution. Accordingly, air from which the biomaterials VR have been removed may be formed as bubbles and discharged through the air discharging pipe 312. For example, a lowermost part of the air injection pipe 311 may be positioned at a lower level than the air discharging pipe 312. Air discharged through the air discharging pipe 312 may be discharged to the outside through the air discharging part 410. According to an embodiment of the inventive concept, since the biomaterials VR included in air are primarily removed by the first processing part 200 and the residual biomaterials VR included in air may be secondarily removed by the second processing part 300, purified air may be discharged to the outside through the air discharging part 410.

The pump 315 may extract a certain amount of the solution from the wet air purifier 340. For example, the pump 315 may be a peristaltic pump. The solution extracted by the pump 315 from the wet air purifier 340 may be delivered to the solution discharging part 320. Accordingly, the solution discharging part 320 may deliver the extracted solution including at least one biomaterial VR to the second monitoring part 370. Here, a solution equivalent to the amount of the extracted solution may be supplied back to the container 310 through a separate solution supplier (not shown).

As the sensor substrate 330 described below is continuously moved, the extracted solution including at least one biomaterial VR analyzed by a nano-optical sensor 350 may be delivered to a second image sensor 360. The second image sensor 360 may capture an image of the biomaterials VR present on the nano-optical sensor 350 to analyze whether the biomaterials VR are present in the extracted solution. In detail, the image captured by the second image sensor 360 may be analyzed by a system, to which an artificial intelligence image analysis method is applied, so as to determine whether the biomaterials VR are present in the extracted solution. For example, the second image sensor 360 may be a complementary metal oxide silicon (CMOS) image sensor.

Figure 5A:
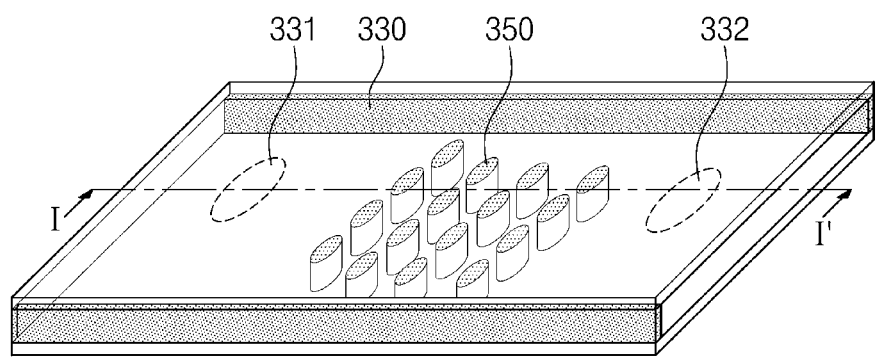
FIGS. 5A and 6A are schematic perspective views illustrating a second monitoring part according to an embodiment of the inventive concept.
Figure 5B:
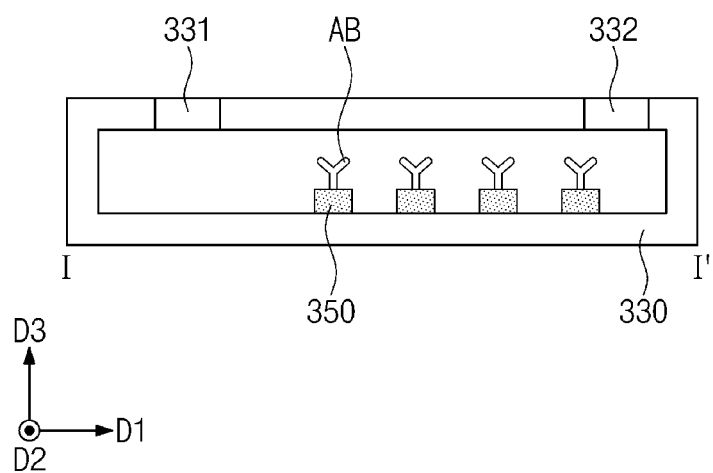
FIGS. 5B, 6B, and 6C are cross-sectional views illustrating a second monitoring part according to an embodiment of the inventive concept, wherein FIG. 5B corresponds to a cross-section taken along line I-I' of FIG. 5A, and FIGS. 6B and 6C correspond to a cross-section taken along line I-I' of FIG. 6A.
Figure 6A:
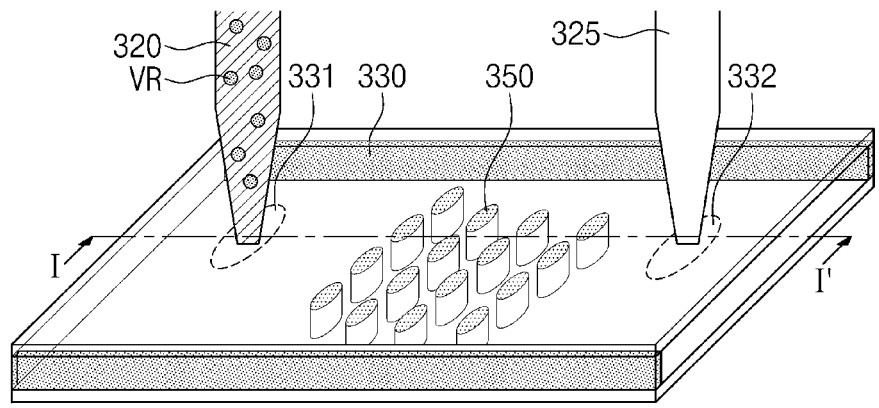
Figure 6B:
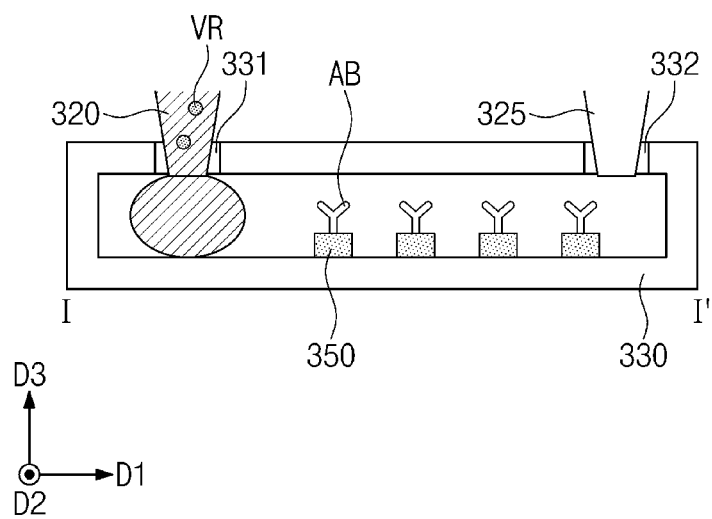
Figure 6C:
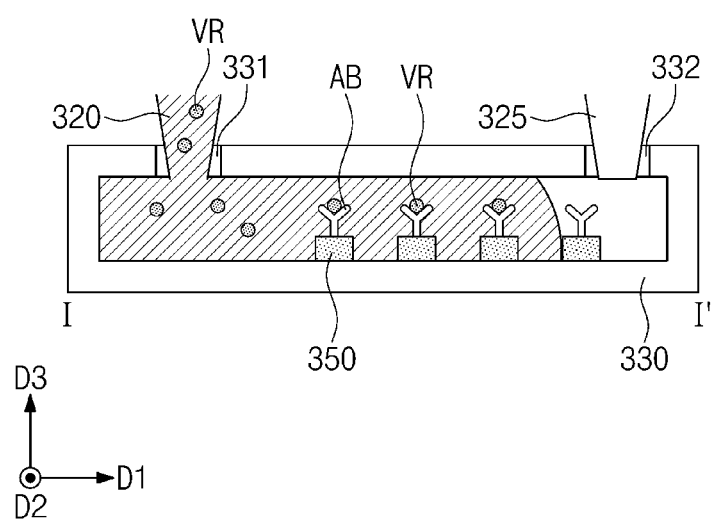

FIGS. 5A and 6A are schematic perspective views illustrating a second monitoring part according to an embodiment of the inventive concept. FIGS. 5B, 6B, and 6C are schematic cross-sectional views illustrating a second monitoring part according to an embodiment of the inventive concept. FIG. 5B corresponds to a cross-section taken along line of FIG. 5A, and FIGS. 6B and 6C each correspond to a cross-section taken along line I-I' of FIG. 6A.

Referring to FIGS. 4, 5A, and 5B, the second monitoring part 370 may include the sensor substrate 330, the nano-optical sensor 350, and the second image sensor 360. The nano-optical sensor 350 may be arranged in the sensor substrate 330. The second image sensor 360 may be arranged on an upper surface of the sensor substrate 330.

The sensor substrate 330 may be a substrate including a vacuum space therein. For example, the sensor substrate 330 may have a form of a cartridge. The sensor substrate 330 is wound in a shape of a roll, and thus may be continuously moved in one direction (e.g., the first direction D1).

The sensor substrate 330 may include, on the upper surface thereof, a first region 331 in which a hole is to be formed by the solution discharging part 320 and a second region 332 in which a hole is to be formed by the air suction part 325.

The nano-optical sensor 350 may be arranged in the vacuum space of the sensor substrate 330. The nano-optical sensor 350 may be arranged in plurality. An antibody AB may be bonded onto an upper surface of the nano-optical sensor 350. For example, each of the antibodies AB may have a shape of Y.

Referring to FIGS. 4, 6A, and 6B, the solution discharging part 320 and the air suction part 325 may be arranged on the sensor substrate 330. For example, the solution discharging part 320 may include a needle structure. The solution discharging part 320 may contact the first region 331 of the sensor substrate 330 and may apply pressure thereto, thereby forming a hole penetrating the first region 331. Accordingly, the extracted solution may be injected into the sensor substrate 330.

The air suction part 325 may include a vent hole. The air suction part 325 may contact the second region 332 of the sensor substrate 330 and may apply pressure thereto, thereby forming a hole penetrating the second region 332. Here, the air suction part 325, which is an empty needle structure, may have a vent hole, and thus may function as a vent hole.

Referring to FIGS. 4, 6A, and 6C, the extracted solution may be moved and cover the nano-optical sensor 350. The antibodies AB may be configured to collect at least one biomaterial VR included in the extracted solution moving in the sensor substrate 330. In detail, the biomaterials VR included in the extracted solution may be combined with the antibodies AB through an antigen-antibody reaction.

Hereinafter, the nano-optical sensor 350 will be described in detail with reference to FIGS. 7A, 7B, 8A, 8B, 9A, 9B, 10A, 10B, 11A, 11B, 12A, 12B, 13A, 13B, 14A, and 14B. However, for convenience, the antibodies AB on the nano-optical sensor 350 are omitted. In some embodiments of the inventive concept, the antibody AB may be bonded onto the nano-optical sensor 350 unlike the illustration.

Figure 7A:
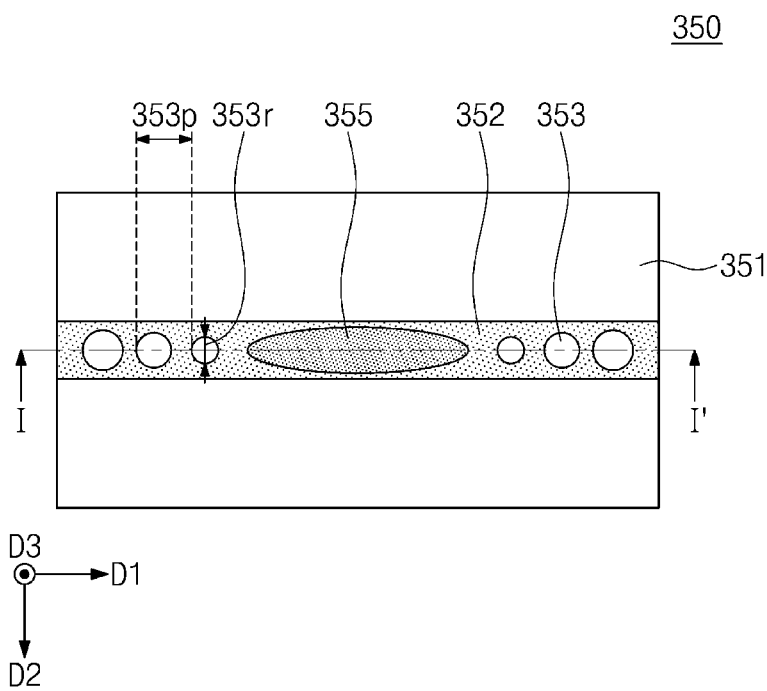
FIGS. 7A and 8A are plan views illustrating a nano-optical sensor according to an embodiment of the inventive concept.
Figure 7B:
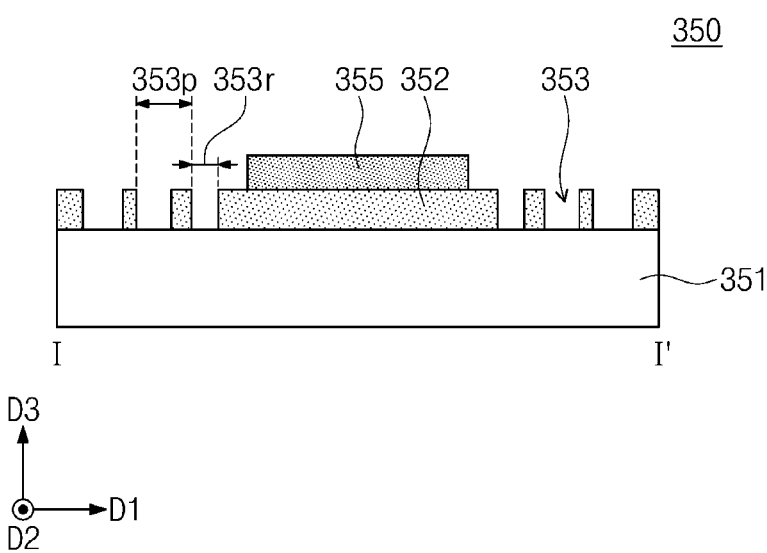
FIGS. 7B and 8B are cross-sectional views illustrating a nano-optical sensor according to an embodiment of the inventive concept, wherein FIG. 7B corresponds to a cross-section taken along line I-I' of FIG. 7A, and FIG. 8B corresponds to a cross-section taken along line I-I' of FIG. 8A.
Figure 8A:
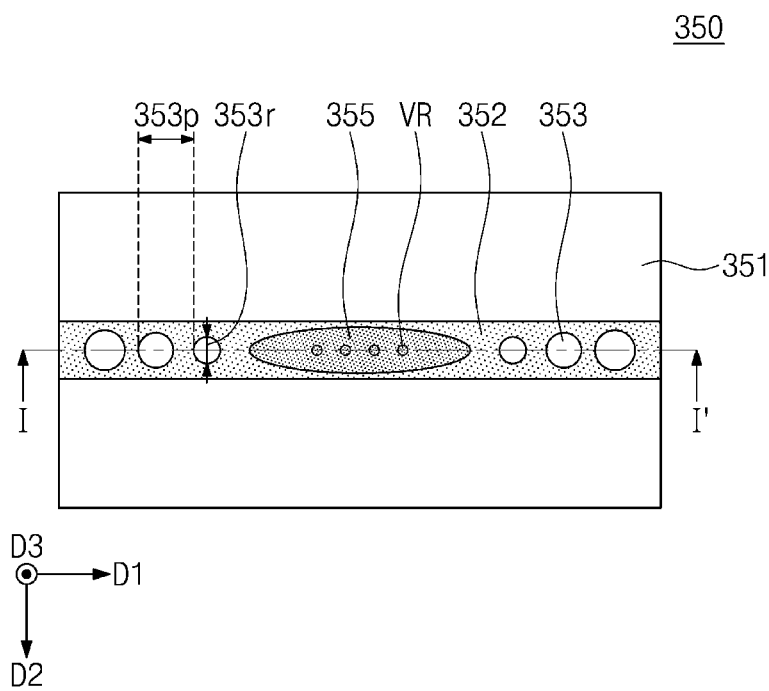
Figure 8B:
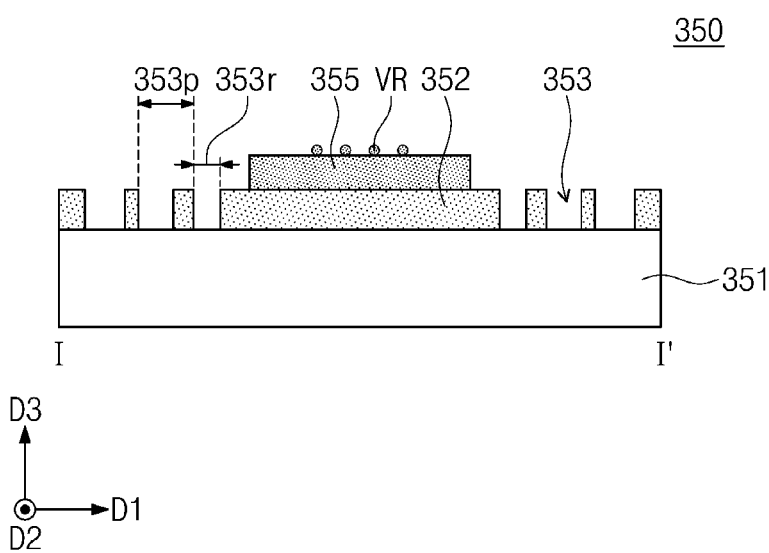

FIGS. 7A and 8A are plan views illustrating a nano-optical sensor according to an embodiment of the inventive concept. FIGS. 7B and 8B are cross-sectional views illustrating a nano-optical sensor according to an embodiment of the inventive concept, wherein FIG. 7B corresponds to a cross-section taken along line I-I' of FIG. 7A, and FIG. 8B corresponds to a cross-section taken along line I-I' of FIG. 8A.

Referring to FIGS. 7A and 7B, the nano-optical sensor 350 may include a substrate 351, a lower layer 352 on the substrate 351, and an upper layer 355 on a partial region of the lower layer 352. An upper surface of the upper layer 355 may have a shape of an ellipse, rectangle, or rhombus of which a length in the first direction D1 is longer than a length in the second direction D2, but an embodiment of the inventive concept is not limited thereto.

The substrate 351 may include, for example, a silicon oxide. The lower layer 352 may include, for example, silicon. The upper layer 355 may include a two-dimensional material. The upper layer 355 may include, for example, at least one of a semiconductor material (e.g., InGaAsP), transition metal dichalcogenide (e.g., $MoS_2$, $MoSe_2$, $WS_2$, $WSe_2$, $MoTe_2$, or $WTe_2$), graphene, or hexagonal boron nitride (hBN).

The lower layer 352 may have, for example, a photonic crystal structure. The upper layer 355 may have, for example, a bound state in the continuum (BIC) structure.

The lower layer 352 may include a plurality of nano-holes 353 penetrating the lower layer 352. The nano-holes 353 may not be provided under the upper layer 355. That is, the nano-holes 353 may not overlap the upper layer 355 in a third direction D3 perpendicular to an upper surface of the substrate 351. The nano-holes 353 may penetrate the lower layer 352 and expose the upper surface of the substrate 351. The nano-holes 353 may be arranged in the first direction D1 and may be spaced apart from each other in the first direction. A diameter 353r of each of the nano-holes 353 may be smaller than a length of the lower layer 352 in the second direction D2. The diameter 353r of each of the nano-holes 353 may be, for example, about 100 nm to about 500 nm. An upper surface of each of the nano-holes 353 may have, for example, a circular or elliptical shape, but an embodiment of the inventive concept is not limited thereto.

The diameter 353r and interval 353p of the nano-holes 353 may not be fixed. For example, the diameter 353r and interval 353p of the nano-holes 353 may decrease in the first direction D1 from one end portion of the lower layer 352 to a center portion of the lower layer 352, and may increase in the first direction D1 from the center portion of the lower layer 352 to another end portion, which faces the one end portion, of the lower layer 352.

A center portion of the nano-optical sensor 350, in which the nano-holes 353 having a relatively small diameter 353r are located, may correspond to a resonator region of a nano-laser. Both end portions of the nano-optical sensor 350, in which the nano-holes 353 having a relatively large diameter 353r are located, may correspond to mirror regions of the nano-laser. In detail, when light is incident on the nano-optical sensor 350, the center portion of the nano-optical sensor 350 may generate resonance, and the both end portions of the nano-optical sensor 350 may reflect light so that the light may be captured by the center portion of the nano-optical sensor 350 without being scattered.

A resonance wave emitted from the center portion of the nano-optical sensor 350 may vary according to arrangement of the nano-holes 353 and the diameter 353r and/or interval 353p of the nano-holes 353. Furthermore, a quality factor of the nano-laser may vary according to a size of the nano-optical sensor 350 and a wavelength of incident light.

Referring to FIGS. 8A and 8B, the extracted solution may be moved, and at least one biomaterial VR included in the extracted solution may be collected on the upper layer 355. Since the at least one biomaterial VR is arranged on the upper layer 355, an effective refractive index of the substrate 351, the lower layer 352, or the upper layer 355 may change. Accordingly, a wavelength of the resonance wave emitted from the nano-optical sensor 350 may change.

Figure 17:
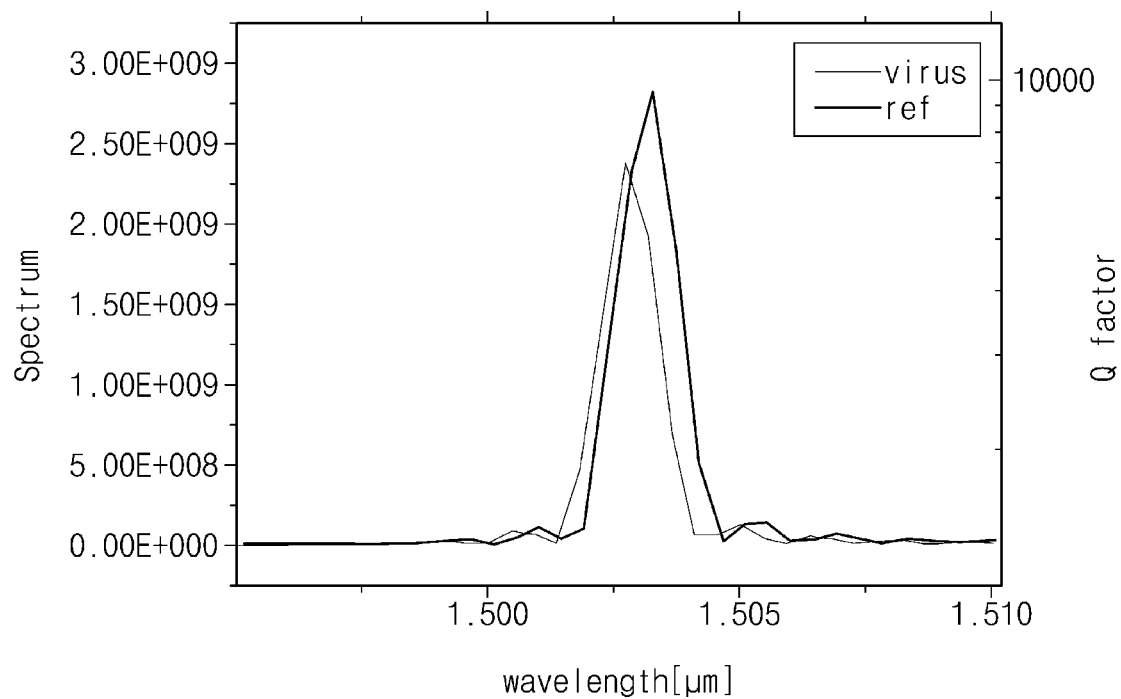
FIG. 17 is a graph showing a result of measuring the wavelength of a resonance wave emitted from a nano-optical sensor according to an embodiment of the inventive concept.

A result of measuring the wavelength of the resonance wave emitted from the nano-optical sensor 350 according to an embodiment of the inventive concept is shown in FIG. 17. Referring to FIG. 17, a resonance wavelength of a comparative example 'ref', in which the biomaterials VR are not present, was measured as about 1503.28 nm. A resonance wavelength of an example 'virus' was measured as about 1502.74 nm, wherein a spherical virus, which is the biomaterial VR having a spherical diameter of about 70 nm and a refractive index RI of about 1.455, is present on the upper layer 355 in the example. Accordingly, whether the biomaterial VR is present may be analyzed on the basis of a change in the wavelength of the resonance wave emitted from the nano-optical sensor 350.

Figure 9A:
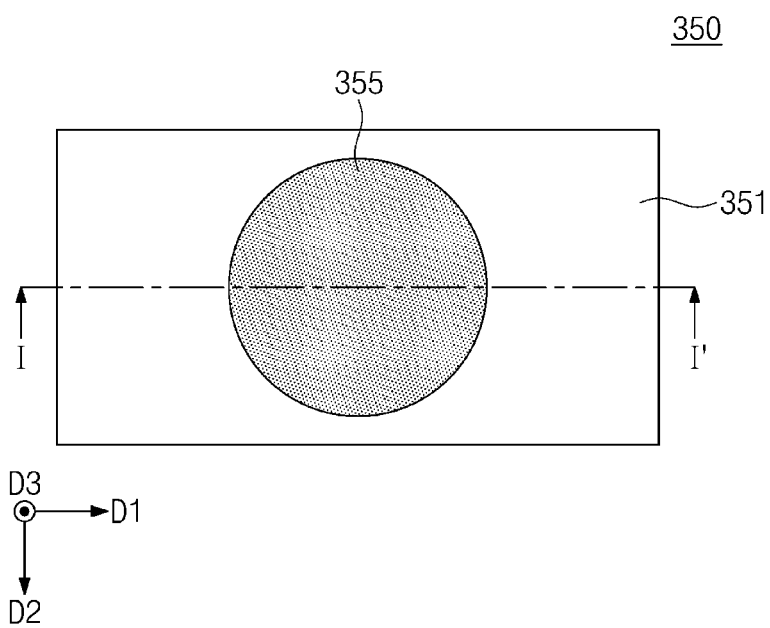
FIGS. 9A and 10A are plan views illustrating a nano-optical sensor according to an embodiment of the inventive concept.
Figure 9B:
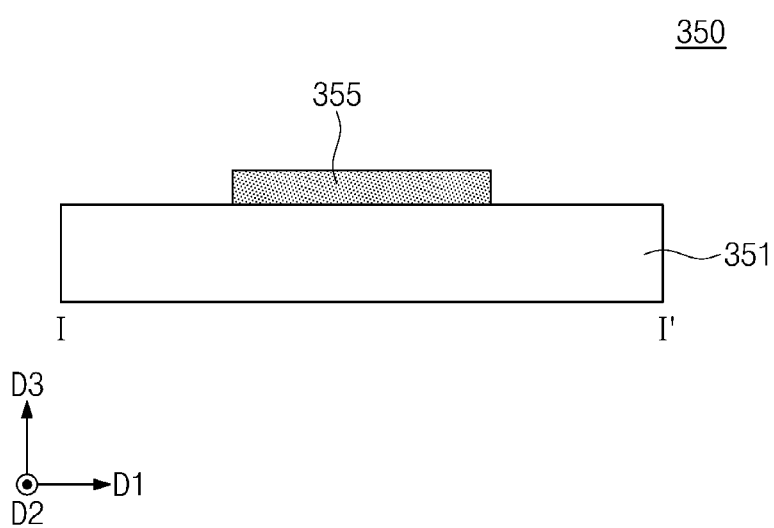
FIGS. 9B and 10B are cross-sectional views illustrating a nano-optical sensor according to an embodiment of the inventive concept, wherein FIG. 9B corresponds to a cross-section taken along line I-I' of FIG. 9A, and FIG. 10B corresponds to a cross-section taken along line I-I' of FIG. 10A.
Figure 10A:
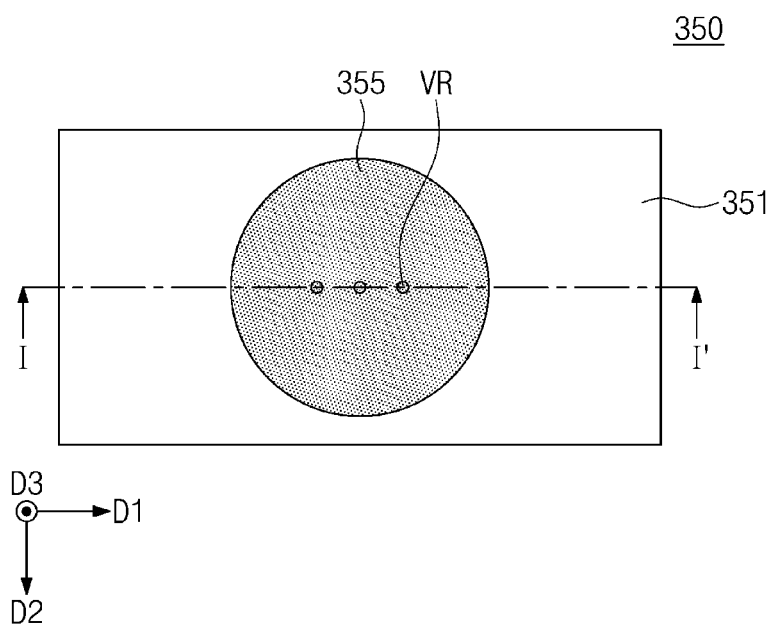
Figure 10B:
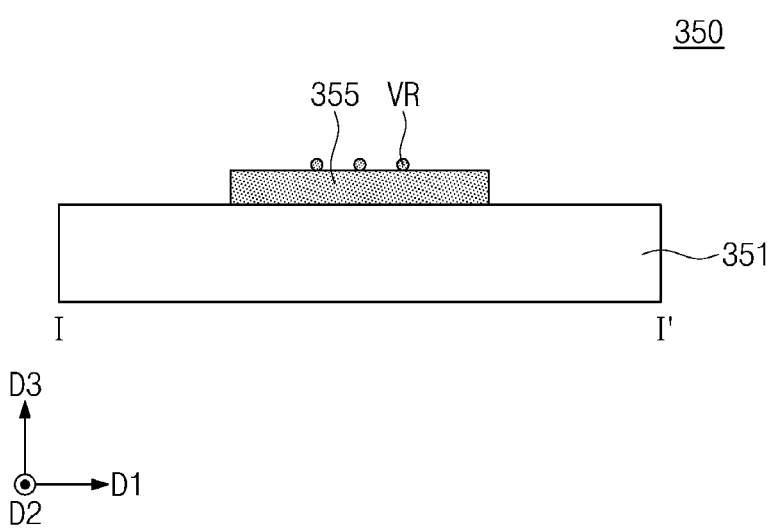

FIGS. 9A and 10A are plan views illustrating a nano-optical sensor according to an embodiment of the inventive concept. FIGS. 9B and 10B are cross-sectional views illustrating a nano-optical sensor according to an embodiment of the inventive concept, wherein FIG. 9B corresponds to a cross-section taken along line I-I' of FIG. 9A, and FIG. 10B corresponds to a cross-section taken along line I-I' of FIG. 10A.

Referring to FIGS. 9A and 9B, the nano-optical sensor 350 may include the substrate 351 and the upper layer 355 on the substrate 351.

The upper layer 355 may have a circular shape in a plan view. That is, the upper layer 355 may have a shape of a disk. For example, the upper layer 355 may be a photonic crystal disk laser. In detail, when light is incident on the nano-optical sensor 350, the nano-optical sensor 350 may generate resonance.

The substrate 351 may include, for example, a silicon oxide. The upper layer 355 may include a two-dimensional material. The upper layer 355 may include, for example, at least one of a semiconductor material (e.g., InGaAsP), transition metal dichalcogenide (e.g., $MoS_2$, $MoSe_2$, $WS_2$, $WSe_2$, $MoTe_2$, or $WTe_2$), graphene, or hexagonal boron nitride (hBN). The upper layer 355 may have, for example, a bound state in the continuum (BIC) structure.

Referring to FIGS. 10A and 10B, the extracted solution may be moved, and at least one biomaterial VR included in the extracted solution may be collected on the upper layer 355. Since the biomaterial VR is arranged on the upper layer 355, an effective refractive index of the substrate 351 or the upper layer 355 may change. Accordingly, a wavelength of the resonance wave emitted from the nano-optical sensor 350 may change. According to an embodiment of the inventive concept, whether the biomaterial VR is present may be analyzed on the basis of a change in the wavelength of the resonance wave emitted from the nano-optical sensor 350.

Figure 11A:
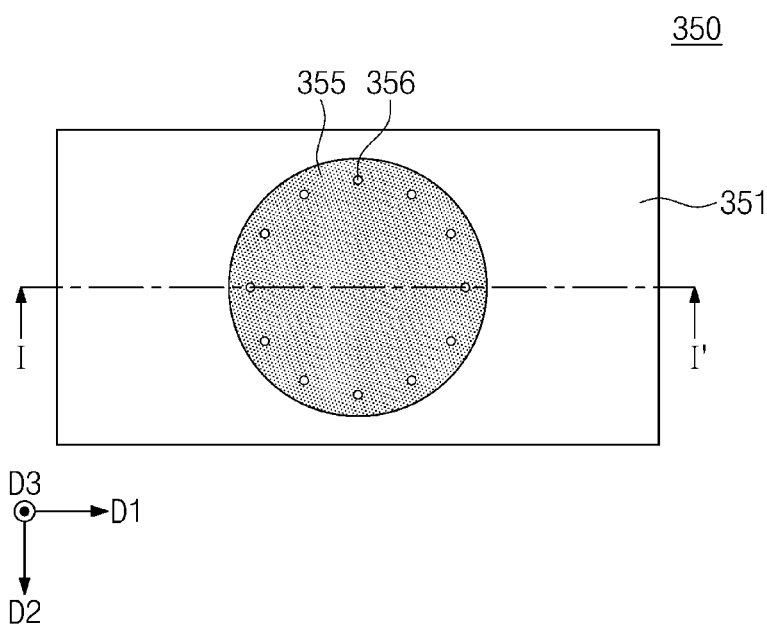
FIGS. 11A and 12A are plan views illustrating a nano-optical sensor according to an embodiment of the inventive concept.
Figure 11B:
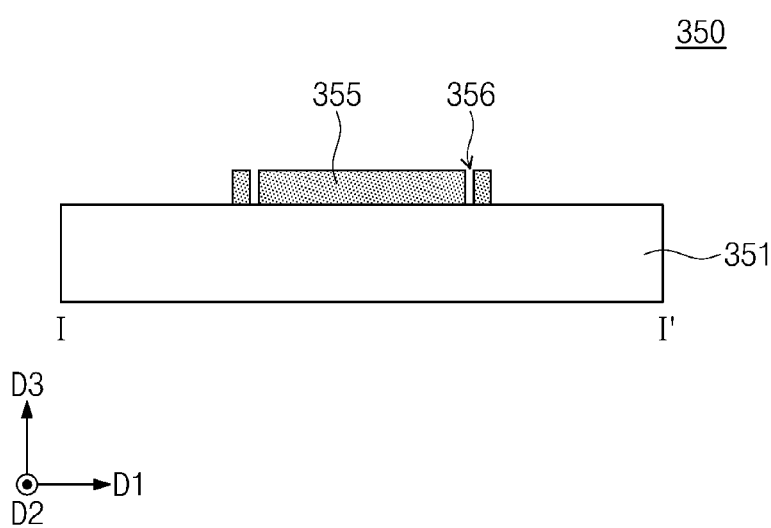
FIGS. 11B and 12B are cross-sectional views illustrating a nano-optical sensor according to an embodiment of the inventive concept, wherein FIG. 11B corresponds to a cross-section taken along line I-I' of FIG. 11A, and FIG. 12B corresponds to a cross-section taken along line I-I' of FIG. 12A.
Figure 12A:
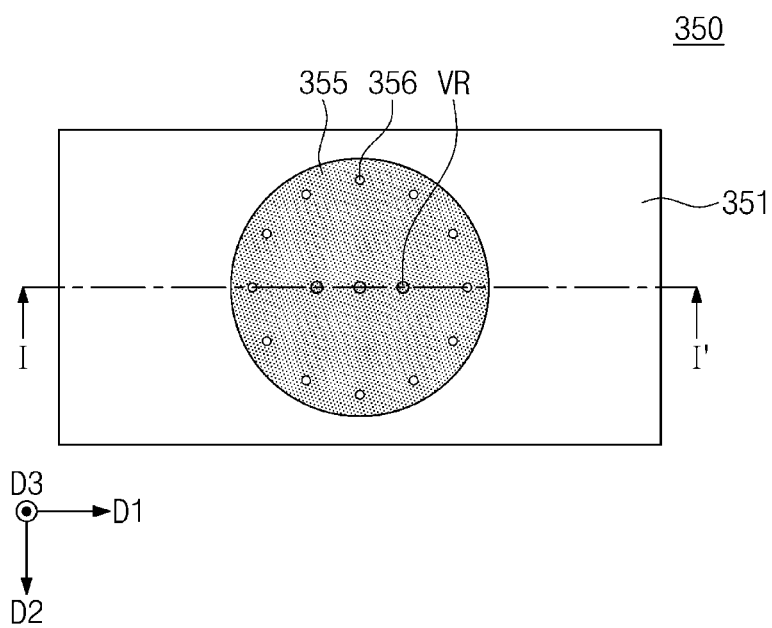
Figure 12B:
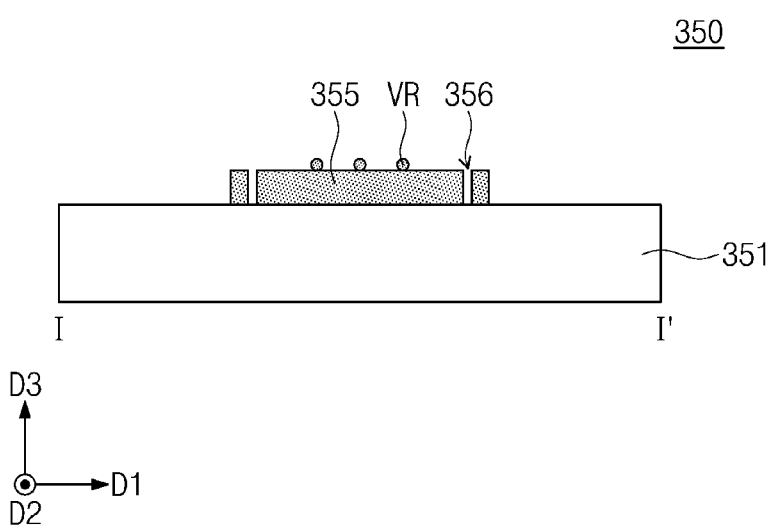

FIGS. 11A and 12A are plan views illustrating a nano-optical sensor according to an embodiment of the inventive concept. FIGS. 11B and 12B are cross-sectional views illustrating a nano-optical sensor according to an embodiment of the inventive concept, wherein FIG. 11B corresponds to a cross-section taken along line I-I' of FIG. 11A, and FIG. 12B corresponds to a cross-section taken along line I-I' of FIG. 12A.

Referring to FIGS. 11A and 11B, the nano-optical sensor 350 may include the substrate 351 and the upper layer 355 on the substrate 351.

The upper layer 355 may include holes 356 penetrating the upper layer 355 and partially exposing the upper surface of the substrate 351. The holes 356 may be arranged adjacent to an outer circumference of the upper layer 355. The upper layer 355 may have a circular shape in a plan view. That is, the upper layer 355 may have a shape of a disk having holes formed therein. For example, the upper layer 355 may be a photonic crystal disk laser. In detail, when light is incident on the nano-optical sensor 350, the nano-optical sensor 350 may generate resonance.

The substrate 351 may include, for example, a silicon oxide. The upper layer 355 may include a two-dimensional material. The upper layer 355 may include, for example, at least one of a semiconductor material (e.g., InGaAsP), transition metal dichalcogenide (e.g., $MoS_2$, $MoSe_2$, $WS_2$, $WSe_2$, $MoTe_2$, or $WTe_2$), graphene, or hexagonal boron nitride (hBN). The upper layer 355 may have, for example, a bound state in the continuum (BIC) structure.

Referring to FIGS. 12A and 12B, the extracted solution may be moved, and at least one biomaterial VR included in the extracted solution may be collected on the upper layer 355. Since the biomaterial VR is arranged on the upper layer 355, an effective refractive index of the substrate 351 or the upper layer 355 may change. Accordingly, a wavelength of the resonance wave emitted from the nano-optical sensor 350 may change. According to an embodiment of the inventive concept, whether the biomaterial VR is present may be analyzed on the basis of a change in the wavelength of the resonance wave emitted from the nano-optical sensor 350.

Figure 13A:
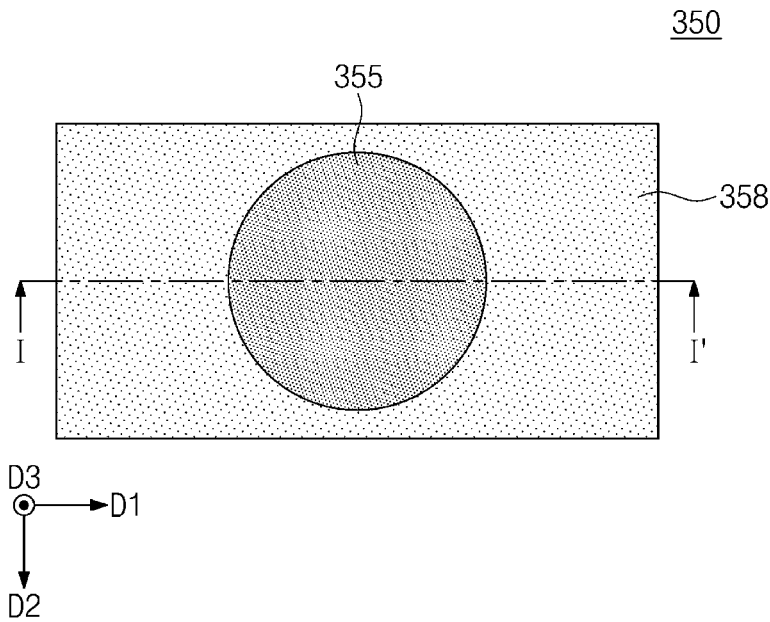
FIGS. 13A and 14A are plan views illustrating a nano-optical sensor according to an embodiment of the inventive concept.
Figure 13B:
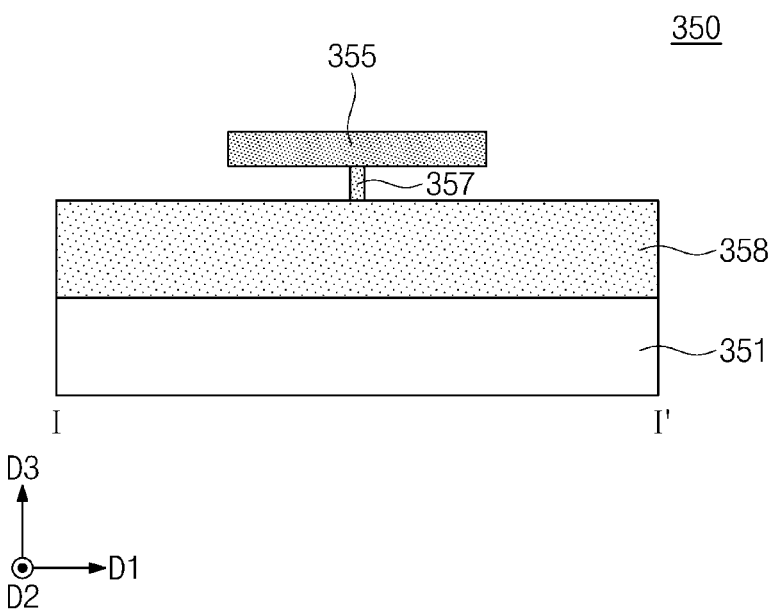
FIGS. 13B and 14B are cross-sectional views illustrating a nano-optical sensor according to an embodiment of the inventive concept, wherein FIG. 13B corresponds to a cross-section taken along line I-I' of FIG. 13A, and FIG. 14B corresponds to a cross-section taken along line I-I' of FIG. 14A.
Figure 14A:
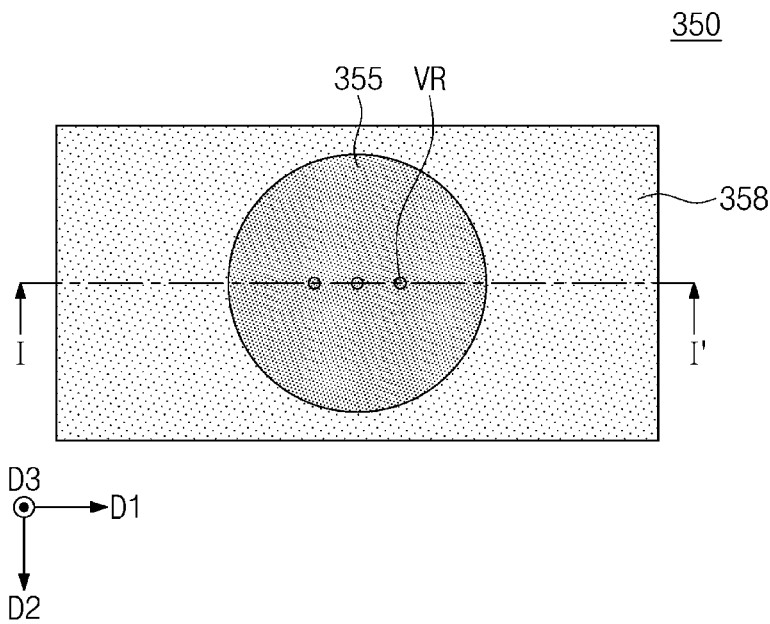
Figure 14B:
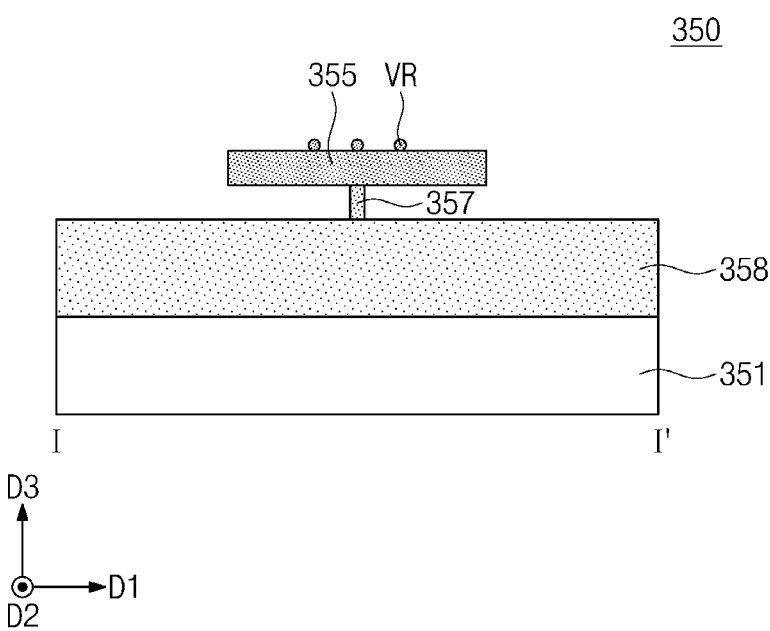

FIGS. 13A and 14A are plan views illustrating a nano-optical sensor according to an embodiment of the inventive concept. FIGS. 13B and 14B are cross-sectional views illustrating a nano-optical sensor according to an embodiment of the inventive concept, wherein FIG. 13B corresponds to a cross-section taken along line I-I' of FIG. 13A, and FIG. 14B corresponds to a cross-section taken along line I-I' of FIG. 14A.

Referring to FIGS. 13A and 13B, the nano-optical sensor 350 may include the substrate 351, an intermediate layer 358 on the substrate 351, the upper layer 355 on the intermediate layer 358, and a support 357 arranged between the intermediate layer 358 and the upper layer 355.

The upper layer 355 may have a circular shape in a plan view. That is, the upper layer 355 may have a shape of a disk. For example, the upper layer 355 may be a photonic crystal disk laser. In detail, when light is incident on the nano-optical sensor 350, the nano-optical sensor 350 may generate resonance.

The support 357 may vertically (e.g., in the third direction D3) overlap a center of the upper layer 355. The support 357 may have a shape of a cylinder or polygonal cylinder.

The substrate 351 may include, for example, indium phosphide (InP). The intermediate layer 358 may include a semiconductor material (e.g., InGaAs). The support 357 may include, for example, indium phosphide (InP). The upper layer 355 may include a two-dimensional material. The upper layer 355 may include, for example, at least one of a semiconductor material (e.g., InGaAsP), transition metal dichalcogenide (e.g., $MoS_2$, $MoSe_2$, $WS_2$, $WSe_2$, $MoTe_2$, or $WTe_2$), graphene, or hexagonal boron nitride (hBN). The upper layer 355 may have, for example, a bound state in the continuum (BIC) structure.

Referring to FIGS. 14A and 14B, the extracted solution may be moved, and at least one biomaterial VR included in the extracted solution may be collected on the upper layer 355. Since the biomaterial VR is arranged on the upper layer 355, an effective refractive index of the substrate 351, the intermediate layer 358, the support 357, or the upper layer 355 may change. Accordingly, a wavelength of the resonance wave emitted from the nano-optical sensor 350 may change. According to an embodiment of the inventive concept, whether the biomaterial VR is present may be analyzed on the basis of a change in the wavelength of the resonance wave emitted from the nano-optical sensor 350.

Figure 15A:
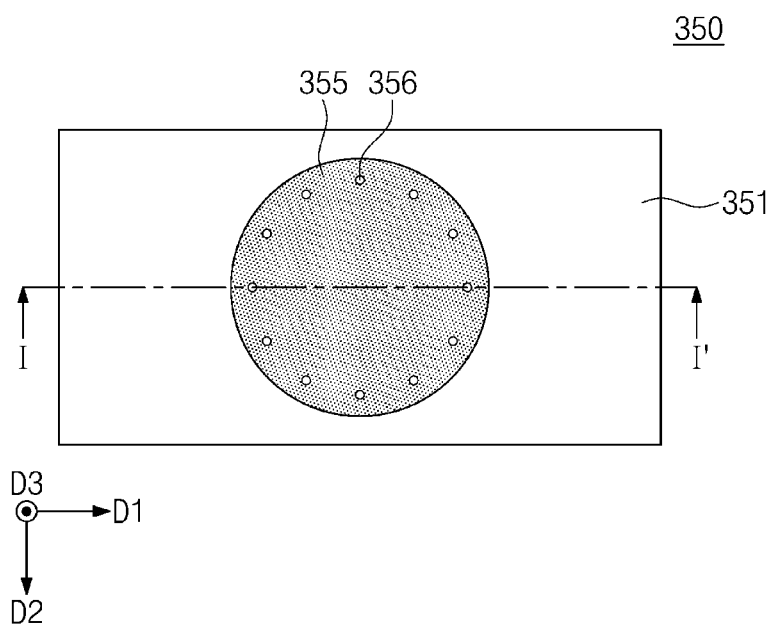
FIGS. 15A and 16A are plan views illustrating a nano-optical sensor according to an embodiment of the inventive concept.
Figure 15B:
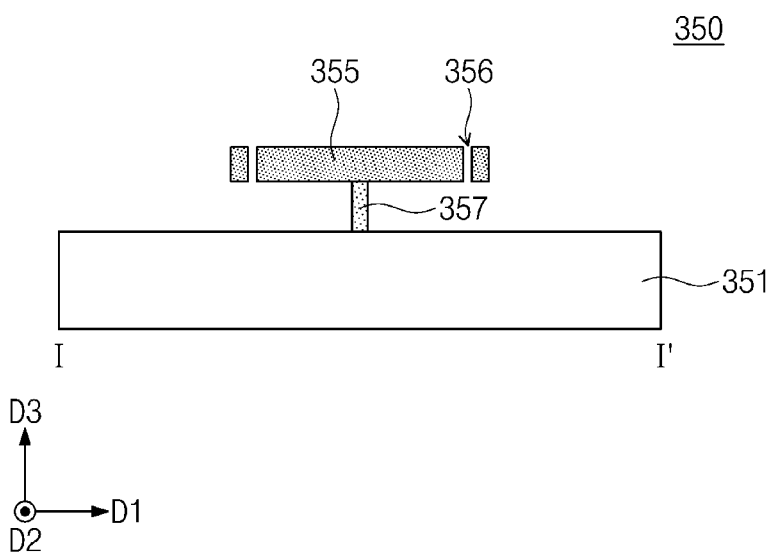
FIGS. 15B and 16B are cross-sectional views illustrating a nano-optical sensor according to an embodiment of the inventive concept, wherein FIG. 15B corresponds to a cross-section taken along line I-I' of FIG. 15A, and FIG. 16B corresponds to a cross-section taken along line I-I' of FIG. 16A.
Figure 15C:
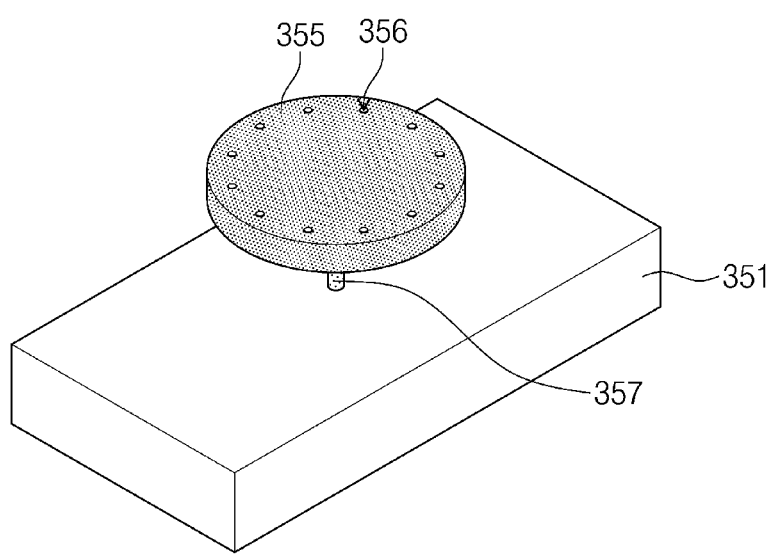
FIG. 15C is a schematic perspective view illustrating a nano-optical sensor according to an embodiment of the inventive concept.
Figure 16A:
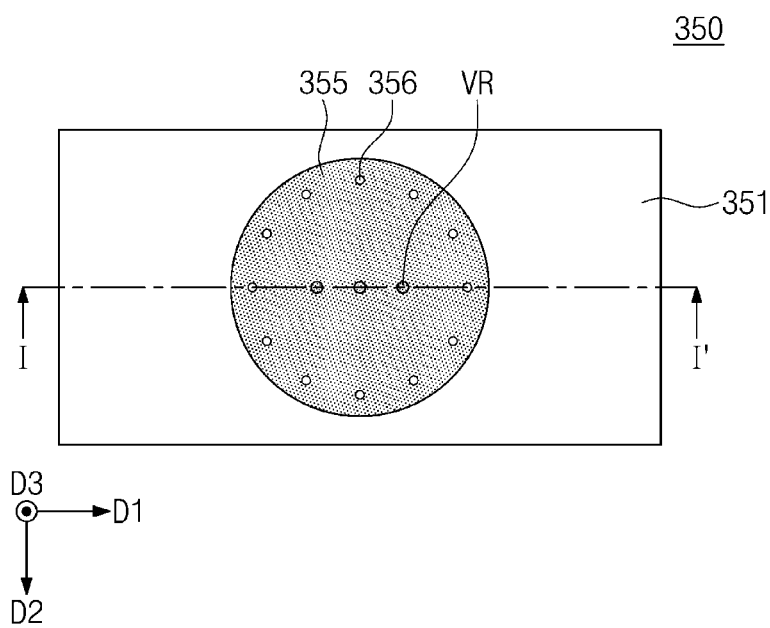
Figure 16B:
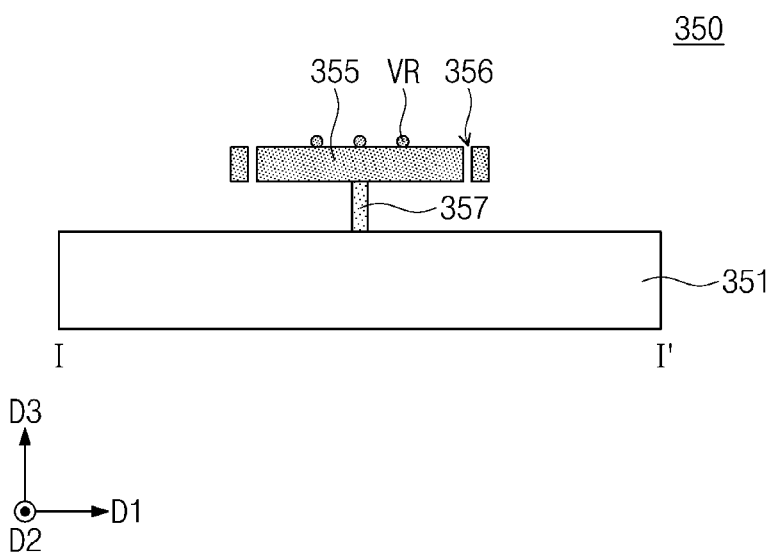

FIGS. 15A and 16A are plan views illustrating a nano-optical sensor according to an embodiment of the inventive concept. FIGS. 15B and 16B are cross-sectional views illustrating a nano-optical sensor according to an embodiment of the inventive concept, wherein FIG. 15B corresponds to a cross-section taken along line I-I' of FIG. 15A, and FIG. 16B corresponds to a cross-section taken along line I-I' of FIG. 16A. FIG. 15C is a schematic perspective view illustrating a nano-optical sensor according to an embodiment of the inventive concept.

Referring to FIGS. 15A, 15B, and 15C, the nano-optical sensor 350 may include the substrate 351, the upper layer 355 on the substrate 351, and the support 357 arranged between the substrate 351 and the upper layer 355.

The upper layer 355 may include holes 356 penetrating the upper layer 355 and partially exposing the upper surface of the substrate 351. The holes 356 may be arranged adjacent to an outer circumference of the upper layer 355. The upper layer 355 may have a circular shape in a plan view. That is, the upper layer 355 may have a shape of a disk having holes formed therein. For example, the upper layer 355 may be a photonic crystal disk laser. In detail, when light is incident on the nano-optical sensor 350, the nano-optical sensor 350 may generate resonance.

The support 357 may vertically (e.g., in the third direction D3) overlap a center of the upper layer 355. The support 357 may have a shape of a cylinder or polygonal cylinder.

The substrate 351 may include, for example, a silicon oxide. The upper layer 355 may include a two-dimensional material. The upper layer 355 may include, for example, at least one of a semiconductor material (e.g., InGaAsP), transition metal dichalcogenide (e.g., $MoS_2$, $MoSe_2$, $WS_2$, $WSe_2$, $MoTe_2$, or $WTe_2$), graphene, or hexagonal boron nitride (hBN). The upper layer 355 may have, for example, a bound state in the continuum (BIC) structure. The support 357 may include, for example, indium phosphide (InP).

Referring to FIGS. 16A and 16B, the extracted solution may be moved, and at least one biomaterial VR included in the extracted solution may be collected on the upper layer 355. Since the biomaterial VR is arranged on the upper layer 355, an effective refractive index of the substrate 351, the upper layer 355, or the support 357 may change. Accordingly, a wavelength of the resonance wave emitted from the nano-optical sensor 350 may change. According to an embodiment of the inventive concept, whether the biomaterial VR is present may be analyzed on the basis of a change in the wavelength of the resonance wave emitted from the nano-optical sensor 350.

According to an embodiment of the inventive concept, clean air may be provided by removing biomaterials that are present in a form of droplets in air through a multi-stage purifying process, and biomaterials such as viruses, bacteria, or the like that may be present in purified air may be monitored in real time.

Although the embodiments of the present invention have been described, it is understood that the present invention should not be limited to these embodiments but various changes and modifications can be made by one ordinary skilled in the art within the spirit and scope of the present invention as hereinafter claimed.

What is claimed is:

1. A biomaterial removing device comprising:
    an air injection part;
    a first processing part spaced apart from the air injection part in a first direction; and
    a second processing part spaced apart from the air injection part with the first processing part therebetween,
    wherein the first processing part comprises a first biomaterial removing part configured to remove biomaterials included in air collected from the air injection part and a first monitoring part configured to analyze residual biomaterials that have passed through the first biomaterial removing part among the biomaterials, and
    the second processing part comprises a second biomaterial removing part configured to remove the residual biomaterials and a second monitoring part configured to analyze whether at least one biomaterial among the residual biomaterials has passed through the second biomaterial removing part,
    wherein the first biomaterial removing part comprises a dry air purifier,
    the second biomaterial removing part comprises a wet air purifier, and
    the first monitoring part and the second monitoring part comprise a first image sensor and a second image sensor, respectively.

2. The biomaterial removing device of claim 1, further comprising rotating parts arranged on both ends of the dry air purifier,
    wherein the dry air purifier is continuously moved due to rotation of the rotating parts, and
    wherein the dry air purifier extends in a second direction intersecting the first direction.

3. The biomaterial removing device of claim 1, wherein the dry air purifier comprises a plurality of laminated nonwoven fabric sheets.

4. The biomaterial removing device of claim 1,
    wherein the wet air purifier comprises a container configured to be provided with a solution, an air injection pipe for injecting air into the solution, and an air discharging pipe, which is connected to the container and discharges air from which the at least one biomaterial among the residual biomaterials has been removed, wherein the at least one biomaterial is collected in the solution.

5. The biomaterial removing device of claim 4, further comprising a solution discharging part and a pump between the container and the solution discharging part.

6. The biomaterial removing device of claim 5, further comprising an air suction part, wherein the solution discharging part delivers an extracted solution in which the at least one biomaterial is collected to the second monitoring part, and wherein the air suction part comprises a vent hole.

7. The biomaterial removing device of claim 1, wherein the second monitoring part further comprises a nano-optical sensor, wherein the nano-optical sensor comprises a substrate and an upper layer.

8. The biomaterial removing device of claim 7, wherein the upper layer comprises at least one of a semiconductor material, transition metal dichalcogenide, graphene, or hexagonal boron nitride (hBN).

9. The biomaterial removing device of claim 7, wherein the upper layer comprises InGaAsP.

10. The biomaterial removing device of claim 7, further comprising a lower layer between the substrate and the upper layer, wherein the lower layer comprises a plurality of nano-holes penetrating the lower layer and partially exposing an upper surface of the substrate.

11. The biomaterial removing device of claim 10, wherein a diameter and interval of the nano-holes change in the first direction.

12. The biomaterial removing device of claim 10, wherein the substrate comprises a silicon oxide, and wherein the lower layer comprises silicon.

13. The biomaterial removing device of claim 7, wherein the upper layer has a circular shape when viewed from directly above the substrate.

14. The biomaterial removing device of claim 13, wherein the upper layer comprises a plurality of holes penetrating the upper layer and partially exposing an upper surface of the substrate, wherein the holes are arranged adjacent to an outer circumference of the upper layer.

15. The biomaterial removing device of claim 7, wherein the second monitoring part further comprises a sensor substrate, wherein the sensor substrate comprises a vacuum space therein, and wherein the nano-optical sensor is arranged in the vacuum space.

16. The biomaterial removing device of claim 1, wherein the first monitoring part further comprises a nozzle into which air that has passed through the first biomaterial removing part is injected, and a transparent substrate on a lower surface of the nozzle, and wherein the first image sensor is disposed on a lower surface of the transparent substrate.

17. The biomaterial removing device of claim 16, wherein the residual biomaterials included in air adhere to an upper surface of the transparent substrate, and wherein the first image sensor captures an image of the residual biomaterials.

18. The biomaterial removing device of claim 1, wherein the first and second image sensors are each a complementary metal oxide silicon (CMOS) image sensor.

19. The biomaterial removing device of claim 1, further comprising a pipe between the air injection part and the first processing part, wherein the air injection part and the first processing part are connected to each other by the pipe.

20. The biomaterial removing device of claim 1, further comprising an air discharging part configured to output, to the outside, air from which the residual biomaterials have been removed by the second processing part.

* * * * *